United States Patent [19]
Gajda et al.

[11] Patent Number: 5,980,859
[45] Date of Patent: Nov. 9, 1999

[54] MODIFIED ZEOLITE BETA PROCESSES FOR PREPARATION

[75] Inventors: Gregory J. Gajda, Mt. Prospect, Ill.; Richard T. Gajek, Daphne, Ala.

[73] Assignee: UOP LLC, Des Plaines, Ill.

[21] Appl. No.: 08/707,063

[22] Filed: Sep. 3, 1996

Related U.S. Application Data

[63] Continuation-in-part of application No. 08/292,665, Aug. 18, 1994, abandoned.

[51] Int. Cl.$^6$ ................................................. C01B 39/08
[52] U.S. Cl. .................................. 423/713; 423/DIG. 27; 502/86
[58] Field of Search ................................. 423/700, 713, 423/714, 716, DIG. 27; 502/85, 86

[56] References Cited

U.S. PATENT DOCUMENTS

| | | |
|---|---|---|
| Re. 28,341 | 2/1975 | Wadlinger et al. . |
| 3,308,069 | 3/1967 | Wadlinger et al. . |
| 3,506,400 | 4/1970 | Eberly, Jr. et al. . |
| 3,591,488 | 7/1971 | Eberly, Jr. et al. ........................ 502/85 |
| 4,093,560 | 6/1978 | Kerr et al. ................................ 423/714 |
| 4,642,226 | 2/1987 | Calvert et al. . |
| 4,923,690 | 5/1990 | Valyocsik et al. . |
| 5,043,307 | 8/1991 | Bowes et al. .............................. 502/86 |
| 5,139,761 | 8/1992 | Nair et al ................................. 502/86 |
| 5,192,727 | 3/1993 | Nair et al. ................................. 502/64 |
| 5,200,168 | 4/1993 | Apelian et al. ......................... 423/714 |
| 5,227,558 | 7/1993 | Shamshoum et al. . |
| 5,256,392 | 10/1993 | Shamshoum et al. .................... 502/86 |
| 5,393,718 | 2/1995 | Skeels et al. ............................. 502/85 |

OTHER PUBLICATIONS

Kiricsi et al., "Progress toward Understanding Zeolite Beta Acidity: An IR and AI NMR Spectroscopic Study," J. Phys. Chem., vol. 98, pp. 4627–4634, 1994.

*Primary Examiner*—Mark L. Bell
*Assistant Examiner*—David Sample
*Attorney, Agent, or Firm*—Thomas K. McBride; Frank S. Molinaro

[57] ABSTRACT

This invention relates to a novel zeolite which has the crystal structure of zeolite beta. The novel zeolite SN-beta has a unique infrared absorbance spectrum, shows enhanced activity for transalkylation of di-isopropyl-benzene and shows less deactivation for cumene synthesis. The zeolite beta is prepared by taking an as-synthesized zeolite beta, steam treating it and then ammonium ion treating it to give a zeolite SN-beta with enhanced catalytic properties.

5 Claims, No Drawings

MODIFIED ZEOLITE BETA PROCESSES FOR PREPARATION

This application is a continuation-in-part of prior copending application U.S. Application No. 08/292,665 filed on Aug. 18, 1994, now abandoned which is incorporated by reference.

FIELD OF THE INVENTION

This invention relates to zeolite beta (hereinafter SN-beta) which has been modified by steam treatment and ammonium ion treatment to give a product with enhanced catalytic properties. Further, this invention also relates to hydrocarbon conversion processes using the zeolite SN-beta.

BACKGROUND OF THE INVENION

Zeolite beta has been known for over twenty years with its synthesis described in U.S. Pat. No. 3,308,069 and Re. 28,341. U.S. Pat. No. 4,923,690 further discloses the preparation of a highly siliceous and partially crystalline zeolite beta. Generally the procedure for preparing zeolite beta is as described in Re 28,341 which is incorporated by reference and which involves a hydrothermal synthesis from a reaction mixture containing sources of silicon, alumina, a templating cation and water. The as-synthesized zeolite beta typically has a chemical composition on an anhydrous basis in terms of molar oxide ratios of $$XM_{2/n}:Al_2O_3:YSiO_2$$

where X has a value from about 0 to about 1.2 and Y has a value from about 20 to about 30.

The as-synthesized zeolite beta can be modified in several ways. For example, it can be dealuminated to provide a zeolite with a higher $SiO_2/Al_2O_3$ ratio or the cations which are contained in the channels of the zeolite can be exchanged for other cations. Applicants have developed a process for modifying an as-synthesized zeolite beta to give a zeolite with unique properties. The process involves first calcining an as-synthesized zeolite beta, then steaming the calcined zeolite and finally treating the steamed zeolite with ammonium ions at a controlled pH of about 1.0 to about 3.5. The resultant zeolite SN-beta is charactertzed by a unique infrared (IR) absorption pattern which has absorbance maxima at 3780–3785 $cm^{-1}$, 3745 $cm^{-1}$ (shoulder), 3735 $cm^{-1}$, 3675 and 3610 $cm^{-1}$, with the 3675 $cm^{-1}$ absorbance being smaller than the $3610^{-1}$ absorbance.

As stated, the art discloses the steaming or dealunination of zeolite beta. Thus, U.S. Pat. No. 5,227,558 discloses steaming a zeolite beta at temperatures of about 550° C. to about 750° C. Further, U.S. Pat. No. 5,139,761 discloses steaming a zeolite omega followed by treating with ammonium ions at low pH. Neither of these references discloses nor hints at applicants' zeolite.

SUMMARY OF THE INVENTION

As stated this invention relates to a crystalline zeolite SN-beta having: 1) a three-dimensional microporous framework structure of $SiO_2$ and $AlO_2$ tetrahedral units; 2) an intracrystalline pore system; and 3) an empirical formula, on an anhydrous basis, expressed as the ratio of the oxides of:

$$aM_{2/n}O:Al_2O_3:bSiO_2$$

where "a" has a value from about zero to about 1.2, M is a cation having a valence of "n" and "b" has a value of about 30 to about 200, the zeolite characterized in that it has the crystal structure of zeolite beta and has absorbance maxima in the infrared region at 3780–3785 $cm^{-1}$, 3745 $cm^{-1}$ (shoulder), 3735 $cm^{-1}$, 3675 $cm^{-1}$, and 3610 $cm^{-1}$, with the 3675 $cm^{-1}$ absorbance being smaller than the 3610 $cm^{-1}$ absorbance and has a surface area of at least 600 $m^2/g$.

Another embodiment of the invention is a process for preparing the zeolite SN-beta described above which comprises a) calcining an as-synthesized zeolite beta starting material at a temperature sufficient to decompose any organic cations contained in the intracrystalline pore system;

b) heating the calcined product of step (a) in the presence of about 5% to about 100% percent steam at a temperature of about 500° C. to about 800° C. for a period of time sufficient to dealuminate and stabilize the structure.

c) contacting the steamed product of step (b) with a sufficient amount of an aqueous solution of ammonium ions at a pH of about 1.0 to about 3.5 for a time sufficient to remove extra framework aluminum and provide said crystalline zeolite SN-beta.

Yet another embodiment is a hydrocarbon conversion process comprising contacting a hydrocarbon feed under hydrocarbon conversion conditions with a catalyst to give a hydroconverted product, the catalyst comprising a crystalline zeolite SN-beta having: 1) a three imensional microporous framework structure of $SiO_2$ and $AlO_2$ tetrahedral units; 2) an intracrystaline pore system; and 3) an empirical formula, on an anhydrous basis, expressed as the ratio of the oxides of:

$$aM_{2/n}O:Al_2O_3:bSiO_2$$

where "a" has a value from about zero to about 1.2, M is a cation having a valence of n and b has a value of about 30 to about 200, the zeolite characterized in that it has the crystal structure of zeolite beta and has absorbance maxima in the infrared region at 3780–3785 $cm^{-1}$, 3745 $cm^{-1}$ (shoulder), 3735 $cm^{-1}$, 3675 $cm^{-1}$, and 3610 $cm^{-1}$, with the 3675 $cm^{-1}$ absorbance being smaller than the 3610 $cm^{-1}$ absorbance and has a surface area of at least 600 $m^2/g$.

DETAILED DESCRIPTION OF THE INVENTION

The starting zeolite used to prepare the novel composition of the present invention is any zeolite beta which can be prepared by means well known in the art such as described in U.S. Pat. Nos. 3,308,069 and 4,642,226, both of which are incorporated by reference. Basically the procedure involves forming a reaction mixture of an aluminum source, a silicon source, an alkali metal compound, an organic templating agent and water. The alumina source may be boehinte alumina, gamma alumina or soluble aluminates, e.g., sodium aluminate or tetraethylammonium aluminates. The silicon source can be silica, silica hydrosol, silicic acid, etc. The alkali metal compound can be sodium hydroxide, lithium hydroxide, potassium hydroxide, etc. Finally, the organic templating agent is usually a quaternary ammonium compound such as tetraethylammonium hydroxide, tetraethylammonium bromide and diethanolamine. The mixture is reacted at temperatures of about 90° C. to about 170° C. for a period of time from about 24 to about 96 hours. The parent zeolite beta is then collected, washed and dried. This parent or as-synthesized zeolite beta will have an empirical formula expressed as molar oxide ratios of $$XM_{2/n}:Al_2O_3:YSiO_2$$

where X has a value from about 0 to about 1.2 and Y has a value from about 20 to about 30.

Regardless of how one obtains a starting zeolite beta, it is treated by the following procedure to give a zeolite SN-beta of this invention. First, the as-synthesized or parent zeolite beta is calcined at a temperature of about 540° C. to about 650° C. for a period of time sufficient to decompose any organic cations contained in the intracrystalline pore system. This time period generally ranges from about 0.5 to about 3 hours. Next, the calcined zeolite beta is heated in the presence of steam in order to remove a fraction of the aluminum from the framework. The steaming is carried out at a temperature of about 500° C. to about 800° C., preferably from about 550° C. to about 700° C., for a period of time from about 1 to about 5 hours in the presence of about 5 to about 100 percent steam. This steaming process will remove aluminum such that the framework ratio of $SiO_2/Al_2O_3$ will be increased to a range of about 30 to about 200.

The final step in the process of this invention involves treating the steamed zeolite beta with an aqueous solution containing ammonium ions. The ammonium ions are derived from ammonium salts such as ammonium nitrate and ammonium chloride and are present in the solution in a concentration from about 5 to about 15 wt %. The aqueous solution also has added to it an acid such as nitric, sulfuric or hydrochloric acid in an amount to give a pH of about 1.0 to about 3.5. This treatment may be carried out at room temperature or elevated temperatures up to about 100° C., preferably 90° C. Finally, the amount of ammonium ion solution relative to the zeolite is not critical but solutions containing from about 20 to about 30 gram ions of $NH_4^+$ per 100 grams of zeolite (anhydrous basis) have been found to be suitable. Although the aqueous solution can be contacted with the zeolite in one step it is more effective to do the treatment in multiple steps, preferably three or more. Optimum conditions of contact time, temperature and concentration of ammonium ions are readily determined for a particular beta starting material by periodically monitoring the physical and chemical properties of the zeolite. Specifically, the water capacity is monitored to determine when the treatment is complete. Treatment is complete when the water adsorption capacity is less than 11.0% when measured at 25° C., a water vapor pressure of 4.6 torr and a time of two hours. The function of the ammonium ion treatment is to help remove non-framework aluminum ions and may also contribute to annealing the structural damage caused by steaming.

The resultant zeolite SN-beta has the following characteristics. First, like the as-synthesized or parent zeolite beta, it has a three dimensional microporous framework structure of $SiO_2$ and $AlO_2$ tetrahedral units along with an intracrystalline pore system. Second, the product zeolite SN-beta has the empirical formula, on an anhydrous basis, expressed as the ratio of the oxides of

$$aM_{2/n}O:Al_2O_3:bSiO_2$$

where "a" has a value from about 0 to 1.2, M is a cation having a valence of "n" and "b" has a value of about 30 to about 200. Third, the zeolite SN-beta product has the crystal structure of zeolite beta which means that it has an x-ray diffraction pattern which contains at least the d-spacings and relative intensities found in Table A.

The interplanar spacings (d) were determined by standard x-ray diffraction techniques. Intensities were determined from the heights of diffraction peaks after subtracting background, "Io" being the intensity of the strongest line or peak, and "I" being the intensity of each of the other peaks.

The relative intensities are reported as very strong (vs), strong (s), medium (m) and weak (w). In terms of 100×I/Io, the above designations are defined as vs=80–100, s=60–80, m=15–60 and w=0–15.

TABLE A

| d (Å) | Relative Intensity |
|---|---|
| 11.5 | strong |
| 4.12 | weak |
| 3.94 | very strong |
| 3.51 | weak |
| 3.29 | weak |

Fourth, the zeolite SN-beta of this invention has a unique infrared (IR) absorbance spectrum characterized by the following absorbance maxima: 3780–3785 cm$^{-1}$, 3745 cm$^{-1}$ (shoulder), 3735 cm$^{-1}$ 3675 and 3610 cm$^{-1}$ with the 3675 cm$^{-1}$ absorbance being smaller than the 3610 cm$^{-1}$ absorbance. The IR spectrum was obtained after pretreating the samples at 400° C. in nitrogen for 1 hour to desorb any volatile compounds that may be present.

Without wishing to be bound by any one particular theory, the following is an interpretation of the IR spectrum. According to Kiricsi, et al. (J. Phys. Chem., 98 (17), 4627–34), these peaks are assigned as follows: 3610 cm$^{-1}$ to strongly acidic bridging hydroxyls, 3660–3680 cm$^{-1}$ to hydroxyl groups bonded to extra-lattice aluminum, 3735 cm$^{-1}$ to internal silanols at framework defects, 3745 cm$^{-1}$ to terminal silanols, and 3780–3785 cm$^{-1}$ to very high frequency hydroxyls bonded to distorted aluminum species that contribute to beta acidity. Finally, the zeolite SN-beta of this invention has a surface area of at least 600 m$^2$/g as determined by the well known B.E.T. method.

Although the zeolite beta of this invention can be used to catalyze various reactions in powder form, it is most advantageous to form the powder into a shaped form by mixing it with a binder such as alumina and then extruding it into shapes such as cylinders, pills, pellets, etc. Extrusion processes are well known in the art and need not be elaborated on here.

Among the processes which can be catalyzed by the zeolite SN-beta of this invention are various hydrocarbon conversion processes such as alkylation and transalkylation of aromatics, cracking, hydrocracking and isomerization of both paraffins and aromatics. Conditions for carrying out the above processes are well known but will be summarized for completeness.

Transalkylation of benzene with di-isopropylbenzene can be carried out either in a batch mode or continuous process with a continuous process being preferred. In a batch mode the reactants and catalyst, i.e., zeolite beta, are heated up to a temperature from about 100° C. to about 250° C. at a pressure sufficient to maintain at least a partial liquid phase. Typically this pressure will be in the range of 250 (1740 kPa) to 1000 psig (6895 kPa) and preferably in the range of about 400 (2758 kPa) to about 600 psig (4137 kPa).

If the process is carried out in a continuous mode, either a fixed bed or moving bed reactor is employed. The fixed bed reactor may be used in an upflow or downflow mode, while the moving bed reactor may be operated in a concurrent or countercurrent catalyst and hydrocarbon flows. The reactors may also contain one or more catalyst beds. A moving bed reactor provides the advantage of continuous spent catalyst removal for regeneration and replacement by fresh or regenerated catalyst. However, it is also possible to carry out the process using swing bed reactors. The temperature and pressure conditions for the continuous process are the same as for the batch mode. The hydrocarbon reactants are contacted with the catalyst for a time sufficient to effect the transalkylation. Typically, this means flowing the hydrocarbons through the bed at a liquid hourly space velocity of about 0.1 to about 10.

The zeolite SN-beta of this invention, which may contain a hydrogenation promoter such as platinum or palladium, can be used to hydrocrack heavy petroleum residual stocks, cyclic stocks and other hydrocrackable charge stocks at temperatures in the range of 400° to 1200° F. (204–649° C.), preferably between 600° and 950° F. (316–510° C.). Reaction pressures are in the range of atmospheric to about 3,500 psig (24,132 kPa g), preferably between 200 and 3000 psig (1379–20,685 kPa g). Contact times usually correspond to liquid hourly space velocities (LHSV) in the range of about 0.1 hr$^{-1}$ to about 10 hr$^{-1}$, preferably between about 0.2 and 3 hr$^{-1}$. Hydrogen circulation rates are in the range of 1,000 to 50,000 standard cubic feet (scf) per barrel of charge (178–8,888 std. m$^3$/m$^3$), preferably between 2,000 and 30,000 scf per barrel of charge (355–5,333 std. m$^3$/m$^3$).

Catalytic cracking processes are preferably carried out with the instant composition using feedstocks such as gas oils, heavy naphthas, deasphalted crude oil residua, etc., with gasoline being the principal desired product. Temperature conditions of 850° to 1100° F. (454° to 593° C.), LHSV values of 0.5 to 10 and pressure conditions of from about 0 to 50 psig (0 to 345 kPa) are suitable.

Isomerization reactions are carried out under the following general conditions of a temperature of 371° C. to 538° C., pressure of about 100 to 500 psig (0.791 to 3.448 MPa), LHSV of 0.1 to 10 hr$^{-1}$ Specifically, olefins are preferably isomerized at temperatures of 500–900° F. (260–482° C.), while paraffins, naphthenes and alkyl aromatics are isomerized at temperatures of 700–1000° F. (371–538° C.). Particularly desirable isomerization reactions contemplated herein include the conversion of n-heptane and/or n-octane to isoheptanes, iso-octanes, butane to iso-butane, methylcyclopentane to cyclohexane, meta-xylene and/or ortho-xylene to para-xylene, 1-butene to 2-butene and/or isobutene, n-hexene to isohexene, cyclohexene to methylcyclopentene, etc. The preferred form of the catalyst is a combination of the instant composition with polyvalent metal compounds (such as sulfides) of metals of Group II-A, Group II-B and rare earth metals.

The following examples are presented in illustration of the invention and are not intended as undue limitations in the generally broad scope of the invention as set out in the appended claims.

EXAMPLE 1

This example presents the preparation of zeolite SN-beta according to the invention. About 2,000 g of zeolite beta prepared according to example 1 of U.S. Pat. No. 5,139,759 was calcined at 600° C. for 90 minutes to remove the organic template. Next, 600 g of the calcined powder was heated at 600° C. in 10% steam for 90 minutes. A second batch (600 g) of calcined zeolite beta was steamed under the same conditions and the two batches were combined.

The calcined and steamed zeolite beta was treated by combining 610 g of zeolite beta and a five liter aqueous solution containing 610 g of NH$_4$NO$_3$ and 244 g of 70% nitric acid, and heating to 85° C. for one hour with stirring. At the end of one hour, the powder was filtered and washed with five liters of deionized water. The above procedure was repeated two more times except that the second solution contained 87 g of 70% nitric acid, while the third treating solution contained 35 g of 70% nitric acid. Finally, the powder was dried at 100° C. for two hours. This final material had a surface area of 680 m$^2$/g, a water capacity of 9.87 wt. % and a Si/Al$_2$ of 55.4. The calcined material exhibits a strong IR band at 3610 cm$^{-1}$, a weak band at 3675 cm$^{-1}$, no shoulder at 3745 cm$^{-1}$ and a very weak band at 3780 cm$^{-1}$. The IR spectrum of the steamed material exhibits a shoulder at 3745 cm$^{-1}$, no band at 3780 cm$^{-1}$, and bands at 3610 cm$^{-1}$ and 3675 cm$^{-1}$ of comparable intensity. The zeolite SN-beta of the invention has an IR spectrum which displays a shoulder at 3745 cm$^{-1}$, a band at 3780 cm$^{-1}$ and a peak at 3610 cm$^{-1}$ much larger than the peak at 3675 cm$^{-1}$.

The zeolite SN-beta powder was next extruded with alumina. In a muller there were placed 448 g of zeolite SN-beta, 45.6 g of pseudoboehinte alumina and 38.3 g gamma-alumina and the mixture mulled for 10 minutes. In a separate mixer there were mixed 182.3 g of boehmite, 70 g water and 64 g of 70% nitric acid, the mixture was mixed until homogeneous and then added to the muller. The resultant mixture was mulled for 20 minutes, followed by addition of 312 g of water and mixing for another 5 minutes. The dough was extruded into $\frac{1}{16}$" extrudates, dried at 100° C. and then calcined at 650° C. for 2 hours. This sample was identified as catalyst A

EXAMPLE 2

Untreated zeolite beta powder prepared as in Example 1 was extruded with alumina by placing in a muller 2435 g of untreated zeolite beta and 356 g of pseudoboehmite alumina and the mixture mulled for 15 minutes. In a separate mixer there were mixed 712 g of boehinte, 1130 g water and 250 g of 70% nitric acid, the mixture was mixed until homogeneous and then added to the muller. The resultant mixture was mulled for 30 minutes, followed by addition of 400 g of water and mixing for another 10 minutes. The dough was extruded into $\frac{1}{16}$" extrudates, dried at 100° C. and then calcined at 540° C. for 2 hours.

A solution of 1300 g of ammonium nitrate in 2.9 gallons of water was prepared. A column was loaded with 1300 g of extrudates and the solution pumped through the extrudates at 85° C. for 10 hours. The extrudates were washed with 11 liters of water, then dried at 100° C. and calcined at 600° C. for 90 minutes. This sample was identified as catalyst B.

EXAMPLE 3

Catalysts A and B were tested for di-isopropylbenzene (DIPB) transalkylation by placing 20 cc of each catalyst in a reactor. A feed consisting of 70% benzene and 30% DIPB by weight was flowed down through the reactor at a pressure of 500 psig and a liquid hourly space velocity (LHSV) of 3 hr$^{-1}$. The results are presented in Table 1.

TABLE 1

| Catalyst I.D. | Temperature (° C.) | DIPB Conversion (%) |
| --- | --- | --- |
| A | 170 | 52 |
| B | 180 | 43 |

The significantly higher conversion at a lower temperature is evidence of the improved activity of the material of the invention. The m-DIPB to p-DIPB molar ratio is 1.8 as compared to an equilibrium value of 2, indicating very slight shape selectivity. By comparison, a zeolite beta prepared according to U.S. Pat. No. 5,227,558 (steamed at 600° C.) and used for ethylbenzene synthesis at 200° C. yields a product with a m-iethylbenzene (DEB) to p-DEB molar ratio of 1.04 (compared to an equilibrium value of 2). Even though the m-DEB is a smaller molecule than m-DIPB, the zeolite beta of U.S. Pat. No. 5,227,558 displays much greater shape selectivity than the zeolite SN-beta of the invention. This demonstrates a fundamental difference in the materials.

EXAMPLE 4

Catalysts A and B were also tested for cumene synthesis by placing 10 cc of each catalyst into a reactor, heating the bed to a maximum temperature of 140° C. A feed stream consisting of benzene and propylene (8:1 molar ratio) was flowed through the reactor at 1000 psig and a LHSV of 6 $hr^{-1}$. The selectivity was measured along with the deactivation rate where the deactivation was calculated by the change in the position of the temperature maximum in the catalyst bed. The percent deactivation is given by:

$$\frac{T_{max}\ location_t - T_{max}\ location_o}{End\ of\ Catalyst\ Bed - T_{max}\ location_o} \times 100\%$$

The rate of deactivation=Percent deactivation/time on stream(t) The results are presented in Table 2.

TABLE 2

| Catalyst I.D. | Cumene Selectivity | Deactivation Rate |
|---|---|---|
| A | 95 | 0 |
| B | 95 | 25 |

This demonstrates the superior stability of the material of the invention. A possible deactivation mechanism is the accumulation of polyalkylate internal to the zeolite. The superior transalkylation activity of the material of the invention would reduce this accumulation and yield a reduced deactivation rate.

EXAMPLE 5

This example reproduces the preparation of zeolite beta reported in U.S. Pat. No. 5,227,558. Zeolite beta was synthesized according to example 1 of U.S. Pat. No. 5,139,759. Ammonium exchange of the as-synthesized zeolite was carried out by preparing a 20 wt. % slurry of the zeolite beta in a solution containing 1.5 lbs. of $NH_4NO_3$ per pound of zeolite beta. This slurry was heated to 90° C. for 4 hours, filtered and washed with one gallon of water per pound of zeolite beta.

The ammonium exchanged zeolite beta was heated at 100° C. for 6 hours and then at 500° C. for 3 hours. Next, the calcined powder was heated in 100% steam at 650° C. for 2 hours. This steamed powder was now treated with nitric acid by preparing a 20 wt. % slurry of the zeolite beta in a 10 wt. % nitric acid solution. This slurry was heated to 50° C. and held there for 90 minutes. The slurry was filtered and washed with ½ gallon of a 2 wt. % $HNO_3$ solution per pound of zeolite beta and then ½ gallon of water per pound of zeolite beta. This acid treatment was repeated to give two ion exchange treatments.

A sample of the finished zeolite beta was analyzed by IR spectroscopy and showed a weak peak at 3780 $cm^{-1}$, a shoulder at 3745 $cm^{-1}$ and a peak at 3735 $cm^{-1}$. This sample did not have peaks at 3675 and 3610 $cm^{-1}$ which are present in the IR spectrum of the composition of the invention as set forth in Example 1. These results clearly indicate that the composition of the '558 reference is different from the composition of the present invention as detailed in Example 1.

We claim as our invention:

1. A crystalline zeolite SN-beta having: 1) a three-dimensional microporous framework structure of $SiO_2$ and $AlO_2$ tetrahedral units; 2) an intracrystalline pore system; and 3) an empirical formula, on an anhydrous basis, expressed as the ratio of the oxides of:

$$aM_{2/n}O:Al_2O_3:bSiO_2$$

where "a" has a value from about zero to about 1.2, M is a cation having a valence of "n" and "b" has a value of about 30 to about 200, the zeolite characterized in that it has the crystal structure of zeolite beta and has absorbance maxima in the infrared region at 3780–3785 $cm^{-1}$, 3745 $cm^{-1}$ (shoulder), 3735 $cm^{-1}$, 3675 $cm^{-1}$, and 3610 $cm^{-1}$, with the 3675 $cm^{-1}$ absorbance being smaller than the 3610 $cm^{-1}$ absorbance and has a surface area of at least 600 $m^2/g$.

2. The zeolite of claim 1 where "b" has a value from about 30 to about 80.

3. A process for preparing a crystalline zeolite SN-beta having: 1) a three-dimensional microporous framework structure of $SiO_2$ and $AlO_2$ tetrahedral units; 2) an intracrystalline pore system; and 3) an empirical formula, on an anhydrous basis, expressed as the ratio of the oxides of:

$$aM_{2/n}O:Al_2O_3:bSiO_2$$

where "a" has a value from about zero to about 1.2, M is a cation having a valence of "n" and "b" has a value of about 30 to about 200, the zeolite characterized in that it has the crystal structure of zeolite beta and has absorbance maxima in the infrared region at 3780–3785 $cm^{-1}$, 3745 $cm^{-1}$ (shoulder), 3735 $cm^{-1}$, 3675 $cm^{-1}$, and 3610 $cm^{-1}$ with the 3675 $cm^{-1}$ absorbance being smaller than the 3610 $cm^{-1}$ absorbance and has a surface area of at least 600 $m^2/g$, the process comprising a) calcining an as-synthesized zeolite beta starting material at a temperature sufficient to decompose any organic cations contained in the intracrystalline pore system;

b) heating the calcined product of step (a) in the presence of about 5 to about 100 percent steam at a temperature of about 500° C. to about 800° C. for a period of time sufficient to dealuminate and stabilize the zeolite.

c) contacting the steamed product of step (b) with a sufficient amount of an aqueous solution of ammonium ions at a pH of about 1.0 to about 3.5 for a time sufficient to remove extraframework aluminum and provide said crystalline zeolite SN-beta.

4. The process of claim 3 where the calcination of step (a) is carried out at a temperature of about 540° C. to about 650° C.

5. The process of claim 3 where in step (b) the temperature is from about 550° C. to about 700° C.

* * * * *